(12) United States Patent
Redler

(10) Patent No.: US 7,641,912 B1
(45) Date of Patent: Jan. 5, 2010

(54) ANTIMICROBIAL COATINGS FOR TREATMENT OF SURFACES IN A BUILDING SETTING AND METHOD OF APPLYING SAME

(75) Inventor: Bryan M. Redler, Andover, MA (US)

(73) Assignee: EnviroCare Corporation, Wilmington, MA (US)

(*) Notice: Subject to any disclaimer, the term of this patent is extended or adjusted under 35 U.S.C. 154(b) by 340 days.

(21) Appl. No.: 10/755,860

(22) Filed: Jan. 12, 2004

Related U.S. Application Data

(60) Provisional application No. 60/439,775, filed on Jan. 13, 2003.

(51) Int. Cl.
*A01N 25/00* (2006.01)
*A01N 25/12* (2006.01)
*A01N 25/26* (2006.01)
*A01N 55/02* (2006.01)
*A01N 55/00* (2006.01)
*A01N 59/00* (2006.01)
*A01N 59/16* (2006.01)

(52) U.S. Cl. .................... 424/405; 424/412; 424/413; 514/495

(58) Field of Classification Search .................. 424/489, 424/617, 618, 405, 412, 413; 514/492, 495, 514/772.3, 772.6, 772.4
See application file for complete search history.

(56) References Cited

U.S. PATENT DOCUMENTS

| | | | |
|---|---|---|---|
| 4,775,585 A | 10/1988 | Hagiwara et al. | |
| 4,906,464 A | 3/1990 | Yamamoto et al. | |
| 4,938,955 A | 7/1990 | Niira et al. | |
| 5,180,585 A | 1/1993 | Jacobson et al. | |
| 5,246,728 A * | 9/1993 | Rodriquez | 427/164 |
| 5,296,238 A * | 3/1994 | Sugiura et al. | 424/604 |
| 5,314,719 A | 5/1994 | Batdorf et al. | |
| 5,562,872 A | 10/1996 | Watanabe | |
| 5,714,430 A | 2/1998 | Gehrer et al. | |
| 5,998,035 A * | 12/1999 | Iwamura et al. | 428/423.1 |
| 6,013,275 A * | 1/2000 | Konagaya et al. | 424/443 |
| 6,160,142 A * | 12/2000 | Sawada et al. | 554/158 |
| 6,248,342 B1 | 6/2001 | Trogolo et al. | |
| 6,248,806 B1 * | 6/2001 | Codolar et al. | 523/177 |
| 6,267,590 B1 | 7/2001 | Barry et al. | |
| 6,296,863 B1 | 10/2001 | Trogolo et al. | |
| 6,365,130 B1 | 4/2002 | Barry et al. | |
| 6,436,422 B1 | 8/2002 | Trogolo et al. | |
| 6,582,715 B1 | 6/2003 | Barry et al. | |
| 6,585,767 B1 | 7/2003 | Holley et al. | |
| 6,663,877 B1 * | 12/2003 | Appleton et al. | 424/411 |
| 6,866,859 B2 | 3/2005 | Trogolo et al. | 424/423 |
| 2002/0068093 A1 * | 6/2002 | Trogolo et al. | 424/618 |
| 2003/0045613 A1 * | 3/2003 | Ohnishi et al. | 524/115 |
| 2003/0096017 A1 * | 5/2003 | Decker et al. | 424/617 |
| 2003/0114622 A1 * | 6/2003 | Masawaki | 526/318 |
| 2003/0118658 A1 * | 6/2003 | Trogolo et al. | 424/490 |
| 2003/0118664 A1 * | 6/2003 | Trogolo et al. | 424/618 |
| 2003/0147966 A1 * | 8/2003 | Franzen et al. | 424/491 |
| 2003/0224169 A1 * | 12/2003 | Kobayashi et al. | 428/408 |
| 2004/0019133 A1 * | 1/2004 | Saito et al. | 523/122 |

FOREIGN PATENT DOCUMENTS

WO    WO 02/18003 A1    3/2002

OTHER PUBLICATIONS

Bennett, H., Practical Emulsions, Chemical Publishing Co., Inc.: 1947, Brooklyn, NY, p. 46.*
Commercial literature regarding Agion Technologies, Inc. viewed from the World Wide Web on Jun. 11, 2004 at http://www.agion-tech.com/Default.asp.

* cited by examiner

*Primary Examiner*—Sreeni Padmanabhan
*Assistant Examiner*—James Henry Alstrum-Acevedo
(74) *Attorney, Agent, or Firm*—Sunstein Kann Murphy & Timbers LLP

(57) ABSTRACT

Antimicrobial coatings to protect surfaces and a method of applying such a coating are disclosed. An antimicrobial coating may be applied to a surface, such as the interior surface of a building's exterior wall. The interior surface must be accessed, and then an antimicrobial coating is provided and applied. The antimicrobial coating includes an inorganic antimicrobial additive and a colloidal polymeric medium. The inorganic antimicrobial additive may be silver, platinum, gold, palladium, copper, zinc, boron, or a compound of any of those elements. By including an ultraviolet tracer or color dye additive in the coating, it is possible to detect the coating at any time, provided that the surface is accessed.

16 Claims, No Drawings

ANTIMICROBIAL COATINGS FOR TREATMENT OF SURFACES IN A BUILDING SETTING AND METHOD OF APPLYING SAME

CROSS REFERENCE TO RELATED APPLICATIONS

This application claims priority from Ser. No. 60/439,775, filed on Jan. 13, 2003, which is herein incorporated entirely by reference.

TECHNICAL FIELD AND BACKGROUND ART

The present invention relates to coatings for surfaces and applying coatings to surfaces, particularly antimicrobial coatings that may be applied to surfaces.

People have long been concerned with protecting themselves from microbes that cause disease, infection, and the growth of bacteria and mold. Making products with antimicrobial additives helps increase protection from microbes. Products containing antimicrobial additives are currently in abundance on the shelves of stores and in consumers' homes, including soaps, lotions, and air fresheners/disinfectants. Such products are used to clean surfaces that may have microbes on them, which offers some protective benefits but does not prevent the microbes from returning. In the field of healthcare, medical devices and dental instruments, as well as various surgical implants, are made with antimicrobial additives to product against the spread of germs and infection. These devices are themselves impervious to microbes. To protect surfaces in the same way, it would be possible to replace the surface entirely, with a new surface that includes antimicrobial additives. However, replacement can be very costly and is not possible in all cases. For example, though costly, it is relatively easy to replace a door or a countertop; it is harder or impossible to replace a wall of a building. Thus, a way of protecting surfaces from microbes that does not require replacing the surface is desirable.

SUMMARY OF THE INVENTION

In a first embodiment of the invention there is provided a method for providing antimicrobial protection to a building, where the building has at least one exterior wall, and the at least one exterior wall has an outer surface and an inner surface. The method includes accessing the inner surface of the at least one exterior wall; providing an antimicrobial treatment including a colloidal polymeric medium, capable of being sprayed onto a surface to establish an antimicrobial polymerical coating; and spraying the antimicrobial treatment on the inner surface, so that such surface has an antimicrobial coating.

In a related embodiment, the building is new construction. In another related embodiment, providing an antimicrobial treatment includes providing an antimicrobial treatment that includes a colloidal polymeric medium at and at least of silver and a silver compound, the treatment capable of being sprayed onto a surface to establish an antimicrobial polymerical coating. Further, the antimicrobial treatment may include microsized silver particles. In another related embodiment the antimicrobial treatment may also include ceramic. In yet another related embodiment, the antimicrobial treatment may also include zinc phosphate.

In yet another related embodiment, providing an antimicrobial treatment may include providing an antimicrobial treatment including a colored dye and a colloidal polymeric medium, capable of being sprayed onto a surface to establish an antimicrobial polymerical coating. Further, the colored dye may be a blue dye.

In still another related embodiment, providing an antimicrobial treatment may include providing an antimicrobial treatment that is translucent and includes a colloidal polymeric medium, capable of being sprayed onto a surface to establish an antimicrobial polymerical coating. Additionally, the method may further include analyzing the antimicrobial treatment on the inner surface with a detecting device to determine if the treatment is present through the presence of the colored dye. Additionally, the detecting device may be an ultraviolet light source.

In another related embodiment, spraying the antimicrobial treatment may include spraying the antimicrobial treatment on the inner surface with a sprayer, so that such surface has an antimicrobial coating. Further, the sprayer may be a high volume low pressure sprayer. Further, the sprayer may include an atomizing tip. In addition, the high volume low pressure sprayer may include an atomizing tip.

In another embodiment, there is provided an antimicrobial coating. The antimicrobial coating includes an inorganic antimicrobial additive, a colloidal polymeric medium, and water. The inorganic antimicrobial additive includes one of the group consisting of silver, platinum, gold, palladium, copper, zinc, boron, and a compound of any of the foregoing elements. In addition, the colloidal polymeric medium may be a polyurethane.

In a related embodiment, the inorganic antimicrobial additive may include a compound comprising silver loaded zirconium phosphate. In addition, the colloidal polymeric medium may be a polyurethane. In addition, the colloidal polymeric medium may be an acrylic. Further, the inorganic antimicrobial additive may include a compound comprising silver loaded zeolite. In addition, the colloidal polymeric medium may be a polyester.

In another related embodiment, the antimicrobial coating may include an ultraviolet stabilizer. Further, the antimicrobial coating may include an anti-settling agent. Further, the antimicrobial coating may include a dispersing agent. Further, the antimicrobial coating may be hydrophilic.

In yet another related embodiment, the antimicrobial coating may include a color dye additive. In addition, the color dye additive may be a blue dye. Further, the antimicrobial coating may include an ultraviolet tracer. Further, the antimicrobial coating may be translucent.

DETAILED DESCRIPTION OF SPECIFIC EMBODIMENTS

Embodiments of the current invention provide a method for providing antimicrobial protection to surfaces, particularly surfaces that require protection from microbes, bacteria, fungus, mold, and the like. Certain embodiments of the current invention are envisioned for protecting the walls of buildings, for example, the inner surfaces of a building's exterior walls. Embodiments may also be used to protect any other surface, including but not limited to countertops, surfaces in food preparation areas such as kitchens, surfaces in bathrooms, doorknobs, door handles, interior and exterior doors, and inner walls, to name but a few.

Various aspects of the present invention are described herein with reference to applying an antimicrobial treatment to the inner surfaces of a building's exterior walls, although it will be apparent that these aspects apply generally to other situations where an antimicrobial treatment may also be used. An exemplary embodiment of the present invention allows antimicrobial protection to be provided to a building, where the building has at least one exterior wall, and the at least one exterior wall has an outer surface and an inner surface. An example of such an inner surface can be seen in FIG. 1. The inner surface of the exterior wall is first accessed. Then, an antimicrobial treatment, capable of being applied to any surface to establish an antimicrobial polymerical coating on that surface, as further described below, is provided. Finally, the antimicrobial treatment is sprayed on the inner surface, so that such surface has an antimicrobial coating.

Thus, the method may be used to apply an antimicrobial treatment to the inner surface of an exterior wall of a building. In particular, the method is especially useful when used in connection with new construction, or a building in the process of being constructed, because accessing the inner surfaces of the exterior walls is simple. The simple access to inner surfaces of exterior walls in new construction can also result in a great cost savings, because such inner surfaces are exposed during the construction process, and no additional steps are needed to access the inner surfaces. Further, when the microbial treatment is applied to new construction, any desired surfaces exposed or installed during the construction process may have the treatment applied to them. These surfaces may include, but are not limited to, doors, door handles or knobs, countertops, and kitchen and bathroom fixtures.

Further, the method as described above may be used to protect both the exterior of walls that exist within the building, including but not limited to ceilings and floors as well. The method is the same as described above. As with accessing the interior of exterior walls during construction, or in a newly constructed house, accessing the exterior portions of such surfaces is simple, requiring only access to the building itself. To use the method on surfaces such as the interior portions of walls that exist within the building, further steps are necessary, such as the removal of floor coverings, drywall, wood, ceiling tiles, and so forth. After these coverings have been removed, however, the method proceeds as described.

Any type of applying device or mechanism may be used to apply the antimicrobial treatment according to the method, for example but not limited to a hand pump sprayer or a paint brush or roller. Preferably, a high volume low pressure sprayer with an atomized tip is used. Such a sprayer provides an appropriate dispersion of the antimicrobial coating, and also increases the efficiency of the amount of treatment used while reducing waste. The application rate of the treatment and how the treatment is applied will depend on the applying device used, the treatment being used, and the surface to which the treatment is applied. For example, to apply one embodiment of the antimicrobial treatment to a wall, a high volume low pressure sprayer may be used, and the treatment is applied at a rate of 2000 square feet per gallon of treatment, in a manner consistent with spray application, to ensure no visible lines of coating on the wall. When applying a different embodiment of the antimicrobial treatment to a different surface, such as a carpet, a pump sprayer may be used, and the treatment is applied at a rate of 2500 square feet per gallon of treatment. In the given example, the coating is sprayed first in one direction going across the rug and then ninety degrees perpendicular to that direction to ensure an appropriate coating thickness, such that the treatment penetrated to the tuft of the fibers. Other application rates and ways of applying the treatment may of course be used, for these or any other surfaces.

The antimicrobial treatment used in the method described above includes a colloidal polymeric medium and an inorganic antimicrobial additive. The treatment may also include water, and may be hydrophilic. The antimicrobial additive is preferably silver, or a silver compound, such as but not limited to a silver salt, silver loaded zirconium phosphate, a silver oxide, or silver loaded zeolite. The antimicrobial additive may also be chosen from the group of platinum, gold, palladium, copper, zinc, boron, and a compound of any of the foregoing elements. The antimicrobial additive may also include ceramic or zinc phosphate.

In various embodiments, silver, alone or in a silver compound, may be in the form of micro sized particles, having a size in the vicinity of 3 microns or smaller. The silver content of the inorganic antimicrobial additive may be up to hundred percent silver.

The colloidal polymeric medium may be any suitable polymer, such as a polyurethane, an acrylic, a polyester, a vinyl, or any blend or combination thereof. The polymeric medium that is used must be colloidal, that is, it should have resin particle sizes within a range of, for example, 0.005-0.015 microns in diameter, and always equal to or smaller than the particles of the inorganic antimicrobial additive that it is to be combined with. The benefit of using colloidal polymer resin particles is such that they are of a size similar to or smaller than the size of the particles of the inorganic antimicrobial additive, to allow a favorable arrangement of the particles within the coating. The smaller size of the colloidal resin particles, when combined with an antimicrobial additive of, for example, silver, facilitates a uniform distribution of the silver and the polymeric resin particles within the dispersion. This relation of relative sizes is believed to assist in causing the silver particles to be exposed at the surface of the dried polymer film. To achieve such distribution, for example, a one hundred percent acrylic coating, comprising a colloidal resin system with particles less than about one micron in size, may be combined with a silver antimicrobial additive comprising ninety-nine percent silver, in the form of particles about three microns in diameter. To test the effectiveness of this treatment, it was then dispersed with a high-shear mixer and blended until uniform. The coating was then spray applied to all sides of twenty-five three inch by four inch by half an inch wood panels by an airless sprayer and allowed to air dry for 1 hour. The samples were then placed in an A.S.T.M. Environmental Chamber inoculated with test organisms, including for purposes of the test, but otherwise not limited to, *Aspergillus Niger* (ATCC 6275), *Penicillium* (ATCC 9849), and *Aureobasidium pullulans* (ATCC 9348). The chamber was then maintained with a relative humidity level of ninety-five percent, temperature of ninety degrees Fahrenheit for a test period duration of, for purposes of the test but otherwise not limited to, 30 days. The test resulted in the highest possible rating of ten, indicating zero visible growth on the coated panels. During the test, twenty-five other uncoated control panels accompanied the coated samples. The uncoated control panels rated between one and five, demonstrating confluent growth.

If the polymer resin particles are larger than the silver particles, the silver particles are believed to be covered by the larger resin particles, with the result that the silver particles are obstructed from exposure at the surface of the dried polymer film. In testing an antimicrobial treatment made in this manner, for example, a one hundred percent acrylic coating comprising a large particle resin system, with particles of 0.015 microns or greater in diameter, was combined with a silver antimicrobial additive comprising ninety-nine percent silver, in the form of particles with a diameter of about three microns, and dispersed with a high-shear mixer and blended until uniform. The resulting treatment was found not to provide antimicrobial protection to the same degree as a treatment using a colloidal polymeric medium. The test treatment, including the noncolloidal polymeric medium, was subjected to the same test as described above (spray applying the treatment to all sides of twenty-five three inch by four inch by half an inch wood panels by an airless sprayer; allowing to air dry for 1 hour; placing the samples in an A.S.T.M. Environmental Chamber inoculated with test organisms *Aspergillus Niger* (ATCC 6275), *Penicillium* (ATCC 9849), and *Aureobasidium pullulans* (ATCC 9348); and maintaining the chamber with a relative humidity level of ninety-five percent and temperature of ninety degrees Fahrenheit for the test period duration of 30 days; twenty-five additional, uncoated control panels accompanied the coated samples). Both coated panels and uncoated control panels had a rating between 1 and 5. The coated panels demonstrated moderate to high visible growth, while the uncoated control panels demonstrated confluent growth. Thus, silver particles should be exposed at the surface of the dried polymer film to properly provide antimicrobial protection.

The antimicrobial treatment may also include other ingredients that provide various benefits and characteristics to the treatment. For example, the treatment may include an ultraviolet stabilizer, an anti-settling agent, a dispersing agent, or an optical marker.

The presence of an optical marker, such as a color dye additive or an ultraviolet tracer, makes it possible to detect the antimicrobial treatment after it has been applied. An optical tracer in the treatment is useful when the antimicrobial treatment is first applied, because it allows the applier to immediately determine whether the surface has been sufficiently covered, either through use of a simple detecting device, or, depending on the marker, visual observation. Use of an optical marker provides quality control to the process of applying the treatment to a surface, because treated surfaces may be readily identified. The surface must be accessed, and a detecting device may be used. For example, if the treatment contains an ultraviolet tracer, an ultraviolet light source may be used to determine if the treatment is still present where applied. Similarly, if the treatment includes a blue colored dye, the presence of the dye may also be detectable by using an ultraviolet light source. An optical marker is also useful after a long period of time has passed from the original application of the treatment, in that a detecting device may be used to detect where the treatment is present and if further antimicrobial treatment needs to be applied.

Examples of antimicrobial treatments that may be used in the embodiments of the current invention may include, but are not limited to, the following:

EXAMPLE 1

A polyurethane coating, 30% solids, with a density of 8.53 lbs/gal, is used with an antimicrobial component including silver loaded zirconium phosphate, where the silver content is 2% by weight solids, and the size of the silver particles is about two to three microns. A high shear mixing of the antimicrobial component with the polyurethane is used to allow for proper dispersion. The resulting treatment was placed in, for example, an HVLP sprayer with, for example, an atomizer tip and, for example, a 0.055 millimeter nozzle, and used to coat painted wood. One gallon of the treatment was added into, for example, a Titan or similar HVLP system, and spray applied at an application rate of 2,000 square feet per gallon. The treatment was applied in a manner consistent with spray paint application to ensure no visible lines of coating on the coated surface. The coating thickness was about 3 microns, and the treatment had a flat sheen. The resulting coating thickness was adequate for the duration requirements of a low wear rate area, such as a painted wall.

EXAMPLE 2

A polyester coating, 33% solids, with a density of 8.48 lbs/gal, is used with an antimicrobial component including silver loaded zeolite, where the silver content is 2% by weight solids, and the size of the silver particles is about two to three microns. A high shear mixing of the antimicrobial component with the polyester is used to allow for proper dispersion. The resulting treatment was placed in a standard hand pump sprayer with an atomizer tip, and used to coat carpet. One gallon of the treatment was added into the standard hand pump sprayer, and spray applied at an application rate of 2,500 square feet per gallon. The treatment was sprayed first in one direction and then 90 degrees perpendicular to that direction, to ensure appropriate coating thickness on the surface and that the treatment penetrated to the tuft of the fibers. The coating thickness was nominally about 3 microns.

EXAMPLE 3

An acrylic coating, 30% solids, with a density of 8.49 lbs/gal, is used with an antimicrobial component including silver loaded zirconium phosphate, where the silver content is 2% by weight solids, and the size of the silver particles is about two to three microns. A high shear mixing of the antimicrobial component with the acrylic is used to allow for proper dispersion using a dispersing blade. The resulting treatment was applied by a roller brush to painted wallboard. One gallon of the treatment was used with no dilution and rolled on the wallboard using standard roller equipment to provide a uniform coating to the wallboard. The coating thickness was about 5 microns, and the treatment had a flat sheen.

The present invention may be embodied in other specific forms without departing from the true scope of the invention. The described embodiments are to be considered in all respects as illustrative only and not restrictive.

What is claimed is:

1. An antimicrobial coating, comprising:
   an inorganic antimicrobial additive material with particles having a diameter of 2 to 3 microns, wherein the inorganic antimicrobial additive material is selected from the group consisting of silver, silver salt, a silver loaded zirconium phosphate, a silver oxide and a silver loaded zeolite;
   a colloidal polymeric medium with polymeric resin particles having a size between 0.005 micron and less than 1 micron in diameter; and
   water.

2. An antimicrobial coating according to claim 1, wherein the colloidal polymeric medium is a polyurethane.

3. An antimicrobial coating according to claim 1, further comprising an ultraviolet stabilizer.

4. An antimicrobial coating according to claim 1, further comprising an anti-settling agent.

5. An antimicrobial coating according to claim 1, further comprising a dispersing agent.

6. An antimicrobial coating according to claim 1, wherein the coating is hydrophilic.

7. An antimicrobial coating according to claim 1, further comprising an ultraviolet tracer.

8. An antimicrobial coating according to claim 1, wherein the coating is translucent.

9. An antimicrobial coating according to claim 1, wherein the resin particles have a size between 0.005 and 0.015 microns in diameter.

10. An antimicrobial coating according to claim 1, wherein the inorganic antimicrobial additive material is a compound of silver, the compound comprising silver loaded zirconium phosphate.

11. An antimicrobial coating according to claim 10, wherein the colloidal polymeric medium is a polyurethane.

12. An antimicrobial coating according to claim 10, wherein the colloidal polymeric medium is an acrylic.

13. An antimicrobial coating according to claim 1, wherein the inorganic antimicrobial additive material is a compound of silver, the compound comprising silver loaded zeolite.

14. An antimicrobial coating according to claim 13, wherein the colloidal polymeric medium is a polyester.

15. An antimicrobial coating according to claim 1, further comprising a color dye additive.

16. An antimicrobial coating according to claim 15, wherein the color dye additive is a blue dye.

* * * * *

UNITED STATES PATENT AND TRADEMARK OFFICE
CERTIFICATE OF CORRECTION

PATENT NO.      : 7,641,912 B1                       Page 1 of 1
APPLICATION NO. : 10/755860
DATED           : January 5, 2010
INVENTOR(S)     : Bryan M. Redler It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 657 days.

Signed and Sealed this

Sixteenth Day of November, 2010

David J. Kappos
*Director of the United States Patent and Trademark Office*